(12) United States Patent
Liu et al.

(10) Patent No.: US 11,360,940 B2
(45) Date of Patent: Jun. 14, 2022

(54) METHOD AND APPARATUS FOR BIOLOGICAL SEQUENCE PROCESSING FASTQ FILES COMPRISING LOSSLESS COMPRESSION AND DECOMPRESSION

(71) Applicant: HUAWEI TECHNOLOGIES CO., LTD., Guangdong (CN)

(72) Inventors: Zhe Liu, Hangzhou (CN); Jun Zhang, Hangzhou (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 489 days.

(21) Appl. No.: 15/993,095

(22) Filed: May 30, 2018

(65) Prior Publication Data

US 2018/0365260 A1   Dec. 20, 2018

Related U.S. Application Data

(63) Continuation of application No. PCT/CN2016/097559, filed on Aug. 31, 2016.

(51) Int. Cl.
*G06F 16/174* (2019.01)
*G16B 50/50* (2019.01)
(Continued)

(52) U.S. Cl.
CPC ......... *G06F 16/1744* (2019.01); *G16B 20/00* (2019.02); *G16B 20/20* (2019.02);
(Continued)

(58) Field of Classification Search
CPC ..... G06F 16/1744; G16B 20/00; G16B 50/00; G16B 30/00; G16B 50/50; G16B 30/10; H03M 7/30; H03M 7/3059; H03M 7/3082
See application file for complete search history.

(56) References Cited

U.S. PATENT DOCUMENTS

| 6,449,764 B1 * | 9/2002 | Sliger ............... G06F 8/658 717/170 |
| 2013/0031092 A1 | 1/2013 | Bhola et al. |

(Continued)

FOREIGN PATENT DOCUMENTS

| CN | 102081707 A | 6/2011 |
| CN | 103559020 A | 2/2014 |

(Continued)

OTHER PUBLICATIONS

Bonfield, et al., Compression of FASTQ and SAM Format Sequencing Data, PLOS One | www.plosone.org, Mar. 2013 | vol. 8 | Issue 3 | pp. 1-11. (Year: 2013).*

(Continued)

*Primary Examiner* — Cheyne D Ly
(74) *Attorney, Agent, or Firm* — Fish & Richardson P.C.

(57) ABSTRACT

This application provides a biological sequence data processing method including selecting a target base from bases in a biological sequence fastq file according to characteristic information of each base. A base patch file is generated by using characteristic information of the target base. Lossless compression is performed on the biological sequence fastq file to obtain a compressed fastq file, and lossless compression is performed on the base patch file to obtain a compressed patch file. The compressed patch file and the compressed fastq file are decompressed. In response to determining that characteristic information of the target base in the decompressed compressed patch file is inconsistent with characteristic information of the target base in the decompressed compressed fastq file, the characteristic information of the target base in the decompressed compressed fastq file is modified to the characteristic information of the target base in the decompressed compressed patch file.

15 Claims, 5 Drawing Sheets

Specification includes a Sequence Listing.

(51) Int. Cl.
  *G16B 50/00* (2019.01)
  *H03M 7/30* (2006.01)
  *G16B 20/00* (2019.01)
  *G16B 20/20* (2019.01)
  *G16B 50/40* (2019.01)
  *G16B 30/00* (2019.01)

(52) U.S. Cl.
  CPC ............ *G16B 50/00* (2019.02); *G16B 50/40* (2019.02); *G16B 50/50* (2019.02); *H03M 7/30* (2013.01); *H03M 7/3059* (2013.01); *G16B 30/00* (2019.02); *H03M 7/3082* (2013.01)

(56) References Cited

U.S. PATENT DOCUMENTS

| | | | |
|---|---|---|---|
| 2013/0166518 A1 | 6/2013 | Mande et al. | |
| 2013/0282677 A1 | 10/2013 | Ji et al. | |
| 2014/0244592 A1 | 8/2014 | Mande et al. | |
| 2015/0227686 A1* | 8/2015 | Sheinin | G16B 30/00 506/35 |

FOREIGN PATENT DOCUMENTS

| | | | | |
|---|---|---|---|---|
| CN | 104008120 | * | 8/2014 | ....... G06F 17/30073 |
| CN | 104008120 A | | 8/2014 | |
| CN | 105760706 A | | 7/2016 | |

OTHER PUBLICATIONS

Shi et al., Reference-based Data Compression for Genome in Cloud, ICCIP '16, Nov. 26-29, 2016, Singapore, pp. 55-59. (Year: 2016).*

Fu et al., LCTD: a Lossless Compression Tool of FASTQ File Based on Transformation of Original File Distribution, 2016 IEEE International Conference on Bioinformatics and Biomedicine (BIBM), pp. 864-869. (Year: 2016).*

Nicolae et al., LFQC: a lossless compression algorithm for FASTQ files, Bioinformatics, 31(20), 2015, 3276-3281. (Year: 2015).*

Bonfield et al., Compression of FASTQ and SAM Format Sequencing Data, PLOS One, Mar. 2013 | vol. 8 | Issue 3, pp. 1-11. (Year: 2013).*

Cock et al., The Sanger FASTQ file format for sequences with quality scores, and the Solexa/Illumina FASTQ variants, Nucleic Acids Research, 2010, vol. 38, No. 6, pp. 1767-1771 (Year: 2010).*

James K. Bonfield et al.: "Compression of FASTQ and SAM Format Sequencing Data", PLOS One, vol. 8, No. 3, Jan. 1, 2013, p. e59190, XP055330942.

Marius Nicolae et al: "LFQC: a lossless compression algorithm for FASTQ files", Bioinformatics., vol. 31, No. 20, Jun. 20, 2015, pp. 3276-3281, XP055512488.

Extended European Search Report issued in European Application No. 16914549.7 dated Oct. 12, 2018, 11 pages.

Skykiker, A Brief Analysis of PostgreSQL Transaction Processing Mechanism. Mysql/postgreSQL, Dec. 16, 2013, Chinaunix, 7 pages.

International Search Report and Written Opinion issued in International Application No. PCT/CN2016/097559 dated Jun. 2, 2017, 14 pages.

Canovas et al., "Lossy compression of quality scores in genomic data," Bioinformatics, vol. 30, No. 15, XP055386522, May 2, 2014, pp. 2130-2136.

EPO Communication pursuant to Article 94(3) EPC issued in European Application No. 16914549.7 dated Sep. 28, 2020, 14 pages.

* cited by examiner

@A819N1ABXX:8:2207:7170:25029/1
TTTAGAATTTTATACGGTGGCTTCTATAGCTCTGTGTGTACCCTTTAATCG
+
GGGGGGGGGGGGGGGGGEGGGGGGG@CDDEDBFDFEEEDFEBE=EBECGDCFF

| Sample name | Size of an original file (MB) | Parameter | Size of a compressed quality score (MB) | Precision (%) | Recall (%) | F-score (%) |
|---|---|---|---|---|---|---|
| ESCC-055B | 12288 | r-block5 | 3686.4 | 99.9 | 99.9 | 99.9 |
| | | p-block1 | 3686.4 | 99.9 | 99.9 | 99.9 |

SEQUENCE LISTING

<160> NUMBER OF SEQ ID NOS: 1

<210> SEQ ID NO 1
<211> LENGTH: 53
<212> TYPE: DNA
<213> ORGANISM: Artificial Sequence
<220> FEATURE:
<223> OTHER INFORMATION: Hypothetical exonic sequence from esophageal
      squamous cell carcinoma

<400> SEQUENCE: 1
tttagaattt tatacggtgg cttctatagc tctgtgtgta caccctttaa tcg            53

METHOD AND APPARATUS FOR BIOLOGICAL SEQUENCE PROCESSING FASTQ FILES COMPRISING LOSSLESS COMPRESSION AND DECOMPRESSION

CROSS-REFERENCE TO RELATED APPLICATIONS

This application is a continuation of international Application No. PCT/CN2016/097559, filed on Aug. 31, 2016, the disclosure of which is hereby incorporated by reference in its entirety.

TECHNICAL FIELD

This application relates to the biotechnology field, and in particular, to a biological sequence data processing method and apparatus.

BACKGROUND

With development of sequencing technologies, a quantity of biological sequences is explosively increased. In 30×-depth sequencing, a size of technical data of whole genome data of one person almost reaches 200 G, and large storage space is occupied. Therefore, storage space of gene data needs to be reduced. In the prior-art solution, storage space of gene data is usually reduced by compressing the gene data. A compression manner includes lossy compression and lossless compression.

Figure 1:
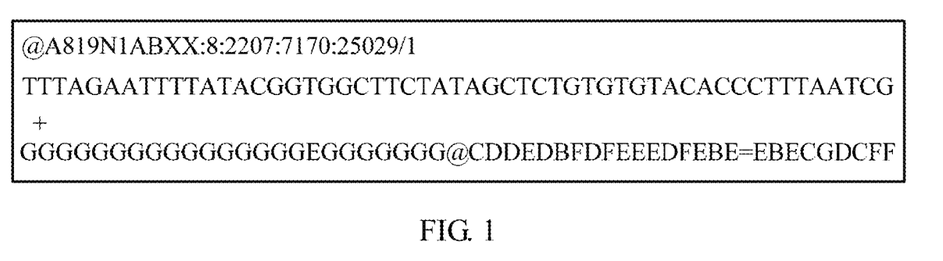
FIG. 1 is a schematic structural diagram of a biological sequence fastq file according to this application (SEQ ID NO:1)

As shown in FIG. 1, FIG. 1 is a schematic structural diagram of a biological sequence fastq file. A name of the fastq file is well-known in the industry. The biological sequence fastq file is used to store a biological sequence (such as a nucleic acid sequence) and corresponding quality evaluation, and includes four parts: a file identifier (read ID), a base sequence (including bases of five types: C, G, A, T, and N), + annotation information, and quality scores. The read ID is used to describe information such as a read name and a sequencing platform. The sequence is used to record a DNA fragment. The quality score is used to indicate a measured credibility degree of each symbol in the base sequence. The read ID, the sequence, and the quality score may be compressed to reduce storage space of the biological sequence fastq file.

Figure 2:
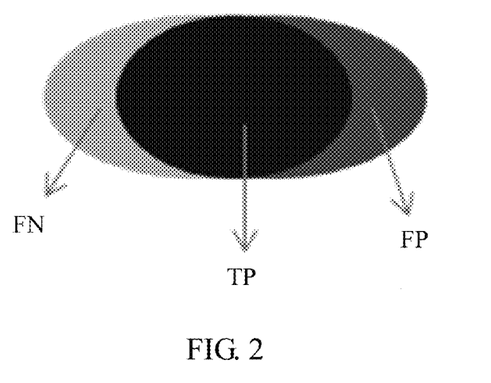
FIG. 2 is a schematic diagram of a correspondence between mutation sites in a VCF file according to this application.

After the biological sequence fastq file is compressed, a visual component framework (VCF) file that includes a mutation site is usually generated by downstream site analysis software by using the compressed biological sequence fastq file, measurement indexes such as precision, recall, and F-score are calculated by analyzing the mutation site, and then site precision of the compressed fastq file is determined. As shown in FIG. 2, FIG. 2 is a schematic diagram of a correspondence between mutation sites in a VCF file. The VCF file is obtained after downstream site analysis software processes a biological sequence fastq file on which lossy compression and lossless compression are performed. False negative (FN) is a quantity of mutation sites in a VCF file generated in lossless compression. False positive (FP) is a quantity of mutation sites in a VCF file generated in lossy compression. True positive (TP) is a quantity of mutation sites existing in both a VCF file generated in lossless compression and a VCF file generated in lossy compression.

It should be noted that, a value of each measurement index such as precision, recall, or F-score ranges from 0 to 1. A larger value indicates higher site precision. Calculation formulas of the measurement indexes such as precision, recall, and F-score are as follows: Precision=TP/(TP+FP), which indicates a quantity of correct results in retrieved results and reflects accuracy (a precision rate); Recall=TP/(TP+FN), which indicates a quantity of retrieved correct results and reflects coverage (a recall rate); and F-score=2*Precision*Recall/(Precision+Recall). F-score is a weighted harmonic mean of precision and recall, and is comprehensively considered when the index precision and the index recall conflict with each other.

Figure 3:
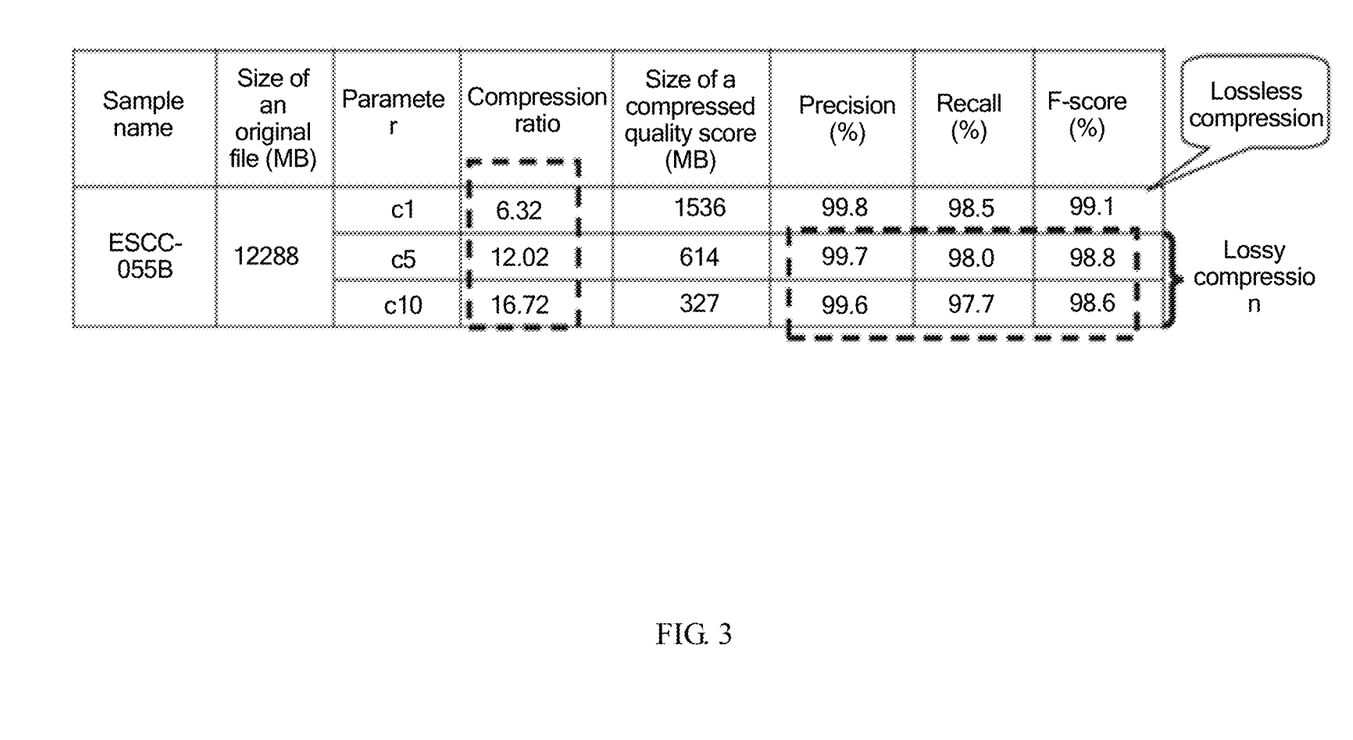
FIG. 3 is a schematic diagram of a compression performance test result according to a prior-art solution.

In a prior-art solution 1, a fastqz compression algorithm is provided. A name of the fastqz compression algorithm is well-known in the industry, and the fastqz compression algorithm supports two compression manners: lossless compression and lossy compression. In lossless compression, a read ID, a sequence, and a quality score are separately encoded. The read ID is encoded in an incremental encoding manner. For the sequence, by default, a quality score of a base N is 33% and a quality score of another base is not 33%. When the sequence is being encoded, the base of the base type N is skipped, and other three bases or four bases are combined into one byte for being encoded. When the sequence is being decoded, a base whose quality score is 33% is set as the base N. For the quality score, a quality score of one base or quality scores of two or three bases are combined into one byte for being encoded. However, actually, there is no correspondence between the base type N and the quality score 33% in a biological sequence fastq file. A quality score of any base may be 33%. Therefore, site precision after compression is not high. In lossy compression, lossy compression is mainly performed on a quality score. Quality scores are graded, and a same grade is replaced with a same quality score. For example, when a parameter is c10, quality scores in [35%, 45%) may be replaced with 35%. As shown in FIG. 3, FIG. 3 is a performance test result obtained after fastqz compression (lossy compression and lossless compression) is performed on exon data of an esophageal squamous cell carcinoma. It can be learned from the performance test result that, although a fastqz compression ratio is extremely high, site precision after compression is not high.

Figure 4:
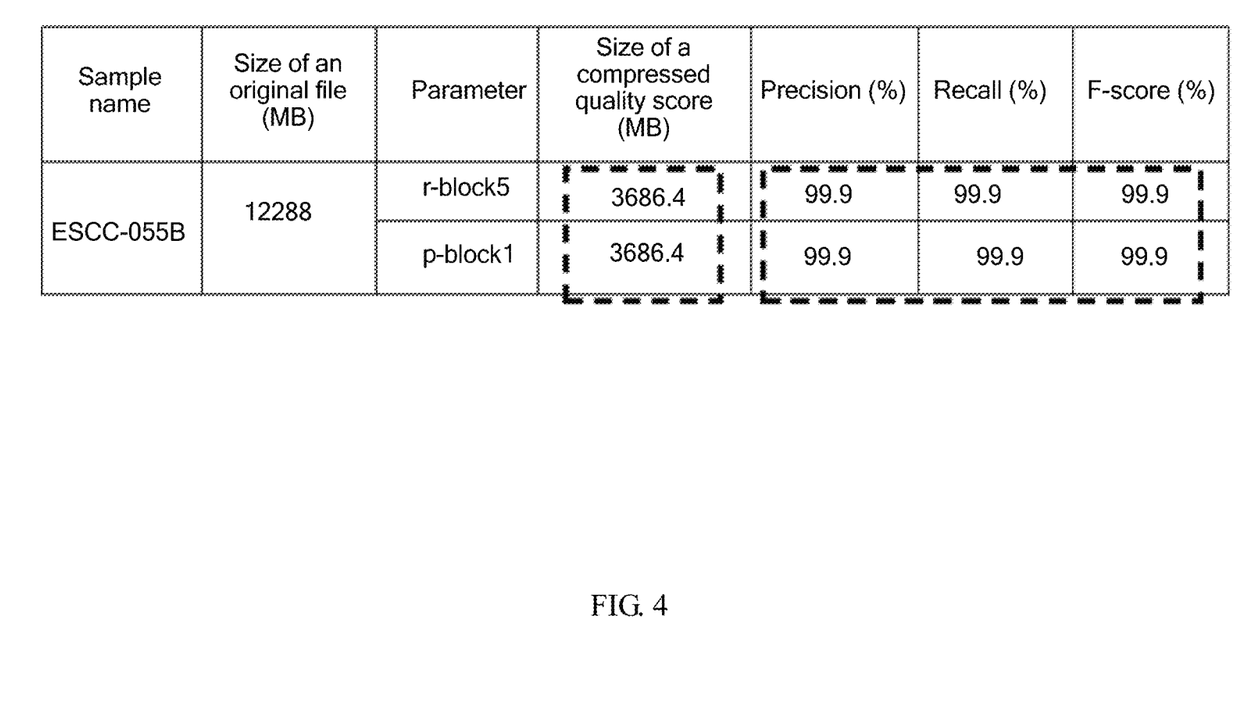
FIG. 4 is a schematic diagram of another compression performance test result according to a prior-art solution.

In a prior-art solution 2, a P-Block/R-Block compression algorithm is provided. Quality scores of a fastq file are independently stored in a block with a variable size in the two algorithms. All quality scores in one block are replaced with a same representative value that does not violate a distortion agreement. A P-Block distortion agreement is Qmax−Qmin<=2p, and an R-Block distortion agreement is Qmax/Qmin<=r2. Qmax and Qmin are respectively a maximum value and a minimum value in quality scores in a block, and p and r are self-defined parameters. As shown in FIG. 4, FIG. 4 is a performance test result obtained after P-Block compression and R-Block compression are separately performed on exon data of an esophageal squamous cell carcinoma. It can be learned from the performance test result that a ratio of compressing quality scores by means of P-Block/R-Block compression is not high.

SUMMARY

This application provides a biological sequence data processing method and apparatus, to resolve problems that a data compression ratio is low and site precision is not high in the prior-art solution.

According to a first aspect, this application provides a biological sequence data processing method, including:

first obtaining characteristic information of each of all bases in a biological sequence fastq file, where the characteristic information includes at least a sequence location and a base type of each base in the biological sequence fastq file; selecting a target base from all the bases according to a preset rule and the characteristic information of each base, and generating a base patch file by using characteristic information of the target base; then performing lossless compression on the biological sequence fastq file to obtain a compressed fastq file, and performing lossless compression on the base patch file to obtain a compressed patch file; finally, separately decompressing the compressed patch file and the compressed fastq file, and checking whether characteristic information of the target base in the decompressed compressed patch file is consistent with characteristic information of the target base in the decompressed compressed fastq file; and if the characteristic information of the target base in the decompressed compressed patch file is inconsistent with the characteristic information of the target base in the decompressed compressed fastq file, modifying the characteristic information of the target base in the decompressed compressed fastq file to the characteristic information of the target base in the decompressed compressed patch file. In this way, the characteristic information of the target base in the decompressed compressed fastq file is adjusted by using the characteristic information of the target base in the decompressed compressed patch file, so that site precision after compression is improved when a compression ratio is ensured.

In a possible design, a base of a target base type is selected from all the bases as the target base, and the base patch file is generated by using a base type and a sequence location of the target base. For example, a base of a base type N is selected, and the base patch file is generated by using the base type N and sequence locations of all bases of the base type N in the biological sequence fastq file. Because a quantity of bases of the base type N is relatively small, a size of the base patch file can be reduced by collecting statistics about characteristic information of the bases of the base type N.

In a possible design, the characteristic information further includes a quality score. A base that is of a target base type and whose quality score is different from a preset threshold and/or a base that is not of the target base type and whose quality score is the preset threshold are/is selected from all the bases as the target base. The base patch file is generated by using a base type, a quality score, and a sequence location that are of the target base. For example, a base that is of a base type N and whose quality score is not q and/or a base that is of another base type and whose quality score is q may be selected from the biological sequence fastq file as the target base. The base patch file is generated by using a quality score, a base type, and a sequence location that are of the target base. Because a quantity of bases of the base type N is relatively small, a size of the base patch file can be reduced by collecting statistics about characteristic information of the base that is of the base type N and whose quality score is not q and the base that is of the another base type and whose quality score is q.

In a possible design, before the characteristic information of each of all the bases in the biological sequence fastq file is obtained, lossy compression may be performed on an original biological sequence fastq file; and an original biological sequence fastq file obtained after the lossy compression is decompressed to obtain the foregoing biological sequence fastq file. A quality score is adjusted after the compressed original biological sequence fastq file is decompressed. According to this method, a compression ratio of the biological sequence fastq file can be further increased.

In a possible design, before the characteristic information of each of all the bases in the biological sequence fastq file is obtained, a quality score in an original biological sequence fastq file may be extracted, and lossy compression is performed on the extracted quality score; and a quality score obtained after the lossy compression is decompressed, and the quality score in the original biological sequence fastq file is replaced with the decompressed quality score to obtain the foregoing biological sequence fastq file. The quality score is adjusted after the decompression. According to this method, a compression ratio of the biological sequence fastq file can be further increased.

In a possible design, before the characteristic information of each of all the bases in the biological sequence fastq file is obtained, lossy compression may be performed on an original biological sequence fastq file; an original biological sequence fastq file obtained after the lossy compression is decompressed to obtain a fastq file in which both a quality score and an identifier read ID are adjusted; and the adjusted quality score is filtered from the fastq file, and a quality score in the original biological sequence fastq file is replaced with the adjusted quality score to obtain the foregoing biological sequence fastq file. According to this method, a compression ratio of the biological sequence fastq file can be further increased.

In another possible design, for the first manner of generating the base patch file, after the compressed patch file and the compressed fastq file are separately decompressed, it may be checked whether a base type corresponding to a sequence location in the decompressed compressed patch file is consistent with a base type corresponding to the sequence location in the decompressed compressed fastq file. If the base type corresponding to the sequence location in the decompressed compressed patch file is inconsistent with the base type corresponding to the sequence location in the decompressed compressed fastq file, the base type corresponding to the sequence location in the decompressed compressed fastq file is modified to the base type corresponding to the sequence location in the decompressed compressed patch file. If the base type corresponding to the sequence location in the decompressed compressed patch file is consistent with the base type corresponding to the sequence location in the decompressed compressed fastq file, the base type corresponding to the sequence location in the decompressed compressed fastq file may not be processed. For example, the compressed patch file includes the sequence locations of all the bases of the base type N. After the compressed patch file and the compressed fastq file are separately decompressed, if a sequence location in the decompressed compressed patch file is corresponding to a base type A, but the sequence location in the decompressed compressed fastq file is corresponding to the base type N, the base type N corresponding to the sequence location in the decompressed compressed fastq file may be modified to the base type A. In this way, a base in the decompressed compressed fastq file is adjusted by using the base patch file, so that site precision of the fastq file is improved.

In another possible design, for the second manner of generating the base patch file, after the compressed patch file and the compressed fastq file are separately decompressed, it may be checked whether a base type and a quality score that are corresponding to a sequence location in the decompressed compressed patch file are consistent with a base type and a quality score that are corresponding to the sequence location in the decompressed compressed fastq file. If the base types are inconsistent, the base type corresponding to the sequence location in the decompressed compressed fastq file is modified to the base type corresponding to the sequence location in the decompressed compressed patch file; and/or if the quality scores are inconsistent, the quality score corresponding to the sequence location in the decompressed compressed fastq file is modified to the quality score corresponding to the sequence location in the decompressed compressed patch file. If the base types are consistent and the quality scores are also consistent, the base type and the quality score that are corresponding to the sequence location in the decompressed compressed fastq file may not be processed. In this way, a base in the decompressed compressed fastq file is adjusted by using the base patch file, so that site precision of the compressed fastq file is improved.

According to a second aspect, this application provides a biological sequence data processing apparatus, and the biological sequence data processing apparatus is configured to implement steps of the biological sequence data processing method provided in the first aspect. The biological sequence data processing apparatus is implemented by hardware/software, and the hardware/software includes units corresponding to the functions.

According to a third aspect, this application provides a biological sequence data processing device, including a processor, a memory, and a communications bus. The communications bus is configured to implement connection and communication between the processor and the memory, and the processor executes a program stored in the memory, to implement steps of the biological sequence data processing method provided in the first aspect.

According to a fourth aspect, this application provides computer readable storage medium, where the computer readable storage medium stores one or more program. The one or more programs include instructions. when at least one processor of a computing device executes the instructions, the computing device performs the biological sequence data processing method described in any one of the first aspect or the optional manners of the first aspect.

BRIEF DESCRIPTION OF DRAWINGS

To describe the technical solutions in the embodiments of this application more clearly, the following briefly describes the accompanying drawings required for describing the embodiments. Apparently, the accompanying drawings in the following description show merely some embodiments of this application, and a person of ordinary skill in the art may still derive other drawings from these accompanying drawings without creative efforts.

DESCRIPTION OF EMBODIMENTS

The following clearly describes the technical solutions in the embodiments of this application with reference to accompanying drawings in the embodiments of this application. Apparently, the described embodiments are merely some but not all of the embodiments of this application. All other embodiments obtained by a person of ordinary skill in the art based on the embodiments of this application without creative efforts shall fall within the protection scope of this application.

Figure 5:
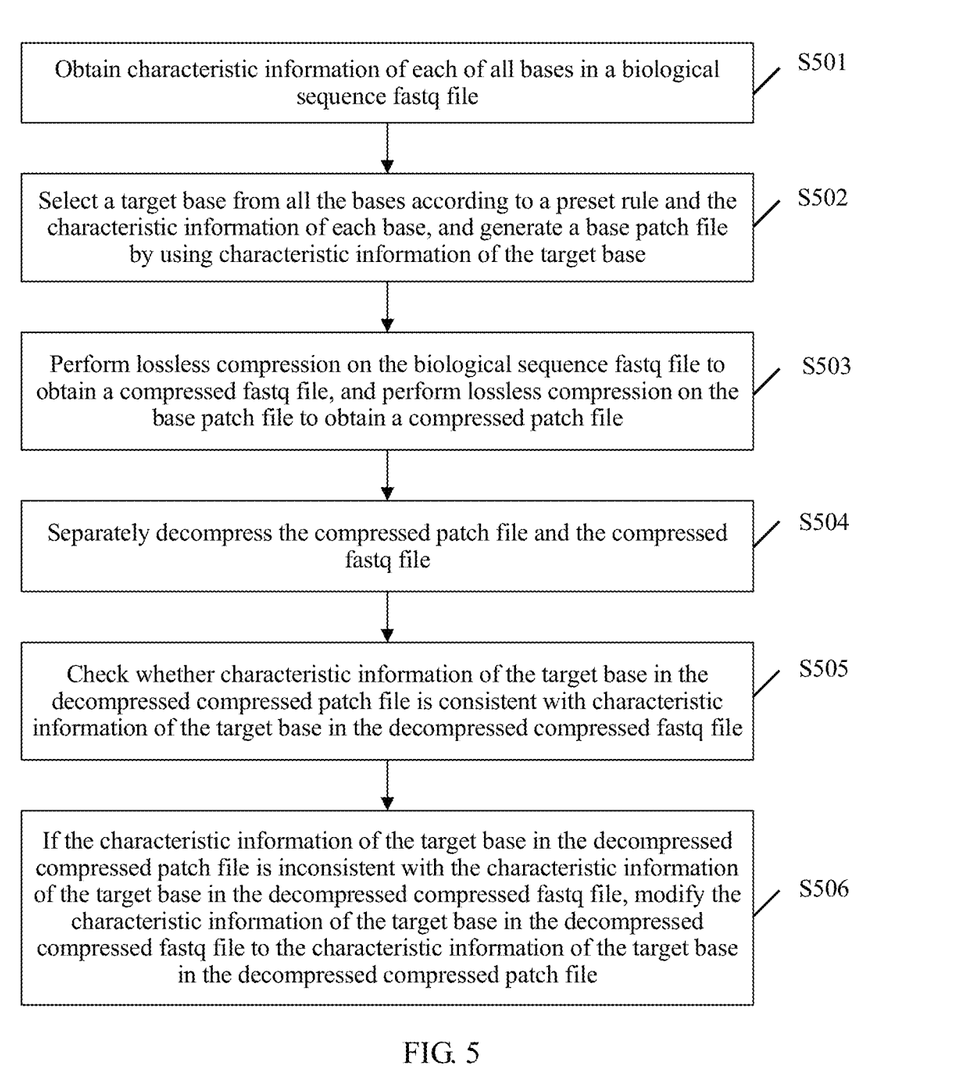
FIG. 5 is a schematic flowchart of a biological sequence data processing method according to an embodiment of this application.

Referring to FIG. 5, FIG. 5 is a schematic flowchart of a biological sequence data processing method according to an embodiment of this application. As shown in the flowchart, the method in this embodiment of this application includes the following steps.

S501. Obtain characteristic information of each of all bases in a biological sequence fastq file, where the characteristic information includes at least a sequence location and a base type of each base in the biological sequence fastq file.

In specific implementation, as shown in FIG. 1, FIG. 1 is a schematic diagram of a biological sequence fastq file according to an embodiment of this application. The biological sequence fastq file includes a file identifier (read ID), a base sequence (Sequence), +annotation information, and quality scores. The base sequence includes bases of five base types: A, T, C, G, and N. The base sequence in the second line is corresponding to the quality scores in the fourth line, and it indicates that each base is corresponding to one quality score. Characteristic information may include a base type of a base and a sequence location of the base in the biological sequence fastq file, or may include a base type of a base, a sequence location of the base in the biological sequence fastq file, and a quality score of the base. The sequence location includes a row coordinate and a column coordinate.

Optionally, before the characteristic information of each of all the bases in the biological sequence fastq file is obtained, lossy compression may be performed on an original biological sequence fastq file; and an original biological sequence fastq file obtained after the lossy compression is decompressed to obtain the foregoing biological sequence fastq file. A quality score is adjusted after the compressed original biological sequence fastq file is decompressed. According to this method, a compression ratio of the biological sequence fastq file can be further increased.

Optionally, before the characteristic information of each of all the bases in the biological sequence fastq file is obtained, a quality score in an original biological sequence fastq file may be extracted, and lossy compression is performed on the extracted quality score; and a quality score obtained after the lossy compression is decompressed, and the quality score in the original biological sequence fastq file is replaced with the decompressed quality score to obtain the foregoing biological sequence fastq file. The quality score is adjusted after the decompression. According to this method, a compression ratio of the biological sequence fastq file can be further increased.

Optionally, before the characteristic information of each of all the bases in the biological sequence fastq file is obtained, lossy compression may be performed on an original biological sequence fastq file; an original biological sequence fastq file obtained after the lossy compression is decompressed to obtain a fastq file in which both a quality score and an identifier read ID are adjusted; and the adjusted quality score is filtered from the fastq file, and a quality score in the original biological sequence fastq file is replaced with the adjusted quality score to obtain the foregoing biological sequence fastq file. According to this method, a compression ratio of the biological sequence fastq file can be further increased.

S502. Select a target base from all the bases according to a preset rule and the characteristic information of each base, and generate a base patch file by using characteristic information of the target base.

In specific implementation, a base of a target base type may be selected from all the bases as the target base, and the base patch file is generated by using a base type and a sequence location of the target base.

For example, a base of a base type N may be selected, and the base patch file is generated by using the base type N and sequence locations of all bases of the base type N in the biological sequence fastq file. Because a quantity of bases of the base type N is relatively small, a size of the base patch file can be reduced by collecting statistics about characteristic information of the bases of the base type N.

Optionally, the characteristic information further includes a quality score. A base that is of a target base type and whose quality score is different from a preset threshold and/or a base that is not of the target base type and whose quality score is the preset threshold may be selected from all the bases as the target base. The base patch file is generated by using a base type, a quality score, and a sequence location that are of the target base. The preset threshold is a standard quality score of a base of the target base type. For example, a base that is of a base type N and whose quality score is not q and/or a base that is of another type and whose quality score is q may be selected from the biological sequence fastq file as the target base. The base patch file is generated by using a base type, a quality score, and a sequence location that are of the base.

For example, a base that is of a base type N and whose quality score is not q and a base that is of another base type and whose quality score is q may be selected from the biological sequence fastq file as the target bases. The base patch file is generated by using a quality score, a base type, and a sequence location that are of the target base. Because a quantity of bases of the base type N is relatively small, a size of the base patch file can be reduced by collecting statistics about characteristic information of the base that is of the base type N and whose quality score is not q and the base that is of the another base type and whose quality score is q, where q may be but is not limited to 33%.

It should be noted that, in this embodiment of this application, the target base may be selected from all the bases according to multiple preset rules. For example, the target base may be selected from the biological sequence fastq file according to a preset base interval. The base patch file is generated by using a sequence location and a base type of the target base, or the base patch file is generated by using a sequence location, a base type, and a quality score that are of the target base. In addition, if several consecutive bases in the biological sequence fastq file are of a same base type, any one of the bases of the same base type may be selected as the target base. The base patch file is generated by using a sequence location and a base type of the target base, or the base patch file is generated by using a sequence location, a base type, and a quality score that are of the target base.

S503. Perform lossless compression on the biological sequence fastq file to obtain a compressed fastq file, and perform lossless compression on the base patch file to obtain a compressed patch file.

In specific implementation, the read ID, the sequence, and the quality score may be separately encoded. The read ID is encoded in an incremental encoding manner. For the sequence, by default, a quality score of a base N is 33% and a quality score of another base is not 33%. When the sequence is being encoded, the base of the base type N is skipped, and other three bases or four bases are combined into one byte for being encoded. For the quality score, a quality score of one base or quality scores of two or three bases are combined into one byte for being encoded. Because a compression ratio is relatively high in this compression algorithm, the compression ratio of the biological sequence fastq file can be increased. In addition, the base patch file may be compressed by using common compression software. For example, the base patch file may be compressed into a compressed patch file in rar or gzip format.

S504. Separately decompress the compressed patch file and the compressed fastq file.

In specific implementation, the compressed patch file and the compressed fastq file may be decompressed by using a method corresponding to S503.

S505. Check whether characteristic information of the target base in the decompressed compressed patch file is consistent with characteristic information of the target base in the decompressed compressed fastq file.

In specific implementation, it may be checked whether a base type corresponding to a sequence location in the decompressed compressed patch file is consistent with a base type corresponding to the sequence location in the decompressed compressed fastq file. If the base type corresponding to the sequence location in the decompressed compressed patch file is consistent with the base type corresponding to the sequence location in the decompressed compressed fastq file, the base type corresponding to the sequence location in the decompressed compressed fastq file may not be processed.

Optionally, it may be checked whether a base type and a quality score that are corresponding to a sequence location in the decompressed compressed patch file are consistent with a base type and a quality score that are corresponding to the sequence location in the decompressed compressed fastq file. If the base types are consistent and the quality scores are also consistent, the base type and the quality score that are corresponding to the sequence location in the decompressed compressed fastq file may not be processed.

S506. If the characteristic information of the target base in the decompressed compressed patch file is inconsistent with the characteristic information of the target base in the decompressed compressed fastq file, modify the characteristic information of the target base in the decompressed compressed fastq file to the characteristic information of the target base in the decompressed compressed patch file. If only characteristic information of some of target bases in the decompressed compressed fastq file is inconsistent with characteristic information of the some of the target bases in the decompressed compressed patch file, only the characteristic information of the some bases in the decompressed compressed fastq file is replaced.

In specific implementation, if the base type corresponding to the sequence location in the decompressed compressed patch file is inconsistent with the base type corresponding to the sequence location in the decompressed compressed fastq file, the base type corresponding to the sequence location in the decompressed compressed fastq file may be modified to the base type corresponding to the sequence location in the decompressed compressed patch file.

For example, the compressed patch file includes the sequence locations of all the bases of the base type N. After the compressed patch file and the compressed fastq file are separately decompressed, if a sequence location in the decompressed compressed patch file is corresponding to a base type A, but the sequence location in the decompressed compressed fastq file is corresponding to the base type N, the base type N corresponding to the sequence location in the decompressed compressed fastq file may be modified to the base type A. In this way, a base in the decompressed compressed fastq file is adjusted by using the base patch file, so that site precision of the fastq file is improved.

Optionally, if both the base type and the quality score that are corresponding to the sequence location in the decompressed compressed patch file are inconsistent with the base type and the quality score that are corresponding to the sequence location in the decompressed compressed fastq file, the base type corresponding to the sequence location in the decompressed compressed fastq file may be modified to the base type corresponding to the sequence location in the decompressed compressed patch file, and the quality score corresponding to the sequence location in the decompressed compressed fastq file may be modified to the quality score corresponding to the sequence location in the decompressed compressed patch file.

For example, the compressed patch file includes a sequence location, a quality score, and a base type of the base N whose quality score is not q and a sequence location, a quality score, and a base type of another base whose quality score is q. If a sequence location 10 in the decompressed compressed patch file is corresponding to a base type A and a quality score 33%, but the sequence location 10 in the decompressed compressed fastq file is corresponding to a base type N and a quality score 34%, it can be learned, by checking, that both the base type and the quality score that are corresponding to the sequence location 10 in the decompressed compressed patch file are different from the base type and the quality score that are corresponding to the sequence location 10 in the decompressed compressed fastq file. In this case, the base type N corresponding to the sequence location 10 in the decompressed compressed fastq file may be replaced with the base type A, and the quality score 34% corresponding to the sequence location 10 in the decompressed compressed fastq file may be replaced with the quality score 33%.

In this embodiment of this application, the characteristic information of each of all the bases in the biological sequence fastq file is first obtained, and the target base is selected from all the bases according to the preset rule and the characteristic information of each base, and the base patch file is generated by using the characteristic information of the target base. Then, lossless compression is performed on the biological sequence fastq file to obtain the compressed fastq file, and lossless compression is performed on the base patch file to obtain the compressed patch file. Finally, the compressed patch file and the compressed fastq file are decompressed, and it is checked whether the characteristic information of the target base in the decompressed compressed patch file is consistent with the characteristic information of the target base in the decompressed compressed fastq file. If the characteristic information of the target base in the decompressed compressed patch file is inconsistent with the characteristic information of the target base in the decompressed compressed fastq file, the characteristic information of the target base in the decompressed compressed fastq file is modified to the characteristic information of the target base in the decompressed compressed patch file. In this way, the characteristic information of the target base in the decompressed compressed fastq file is adjusted by using the characteristic information of the target base in the decompressed compressed patch file, so that site precision after compression is improved when a compression ratio is ensured.

Figure 6:
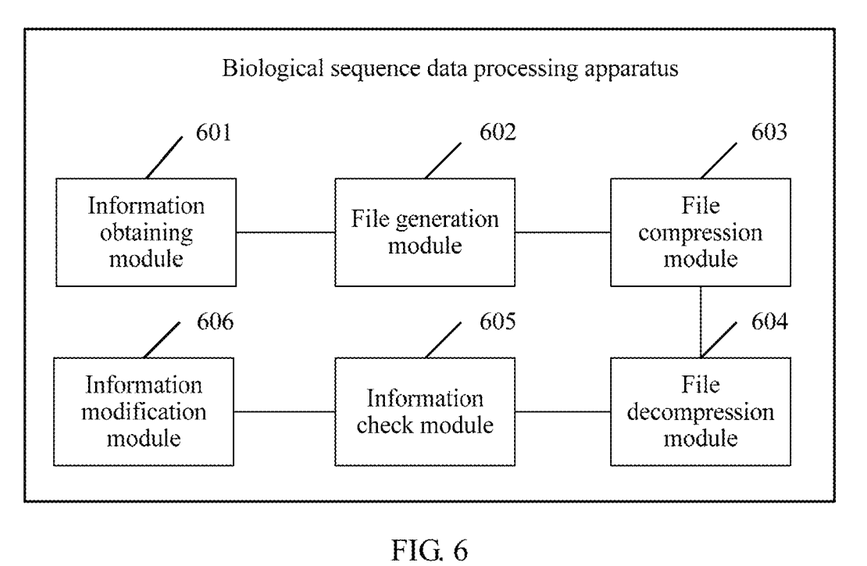
FIG. 6 is a schematic structural diagram of a biological sequence data processing apparatus according to an embodiment of this application.

Referring to FIG. 6, FIG. 6 is a schematic structural diagram of a biological sequence data processing apparatus according to an embodiment of this application. As shown in the diagram, the apparatus in this embodiment of this application includes:

An information obtaining module 601 is configured to obtain characteristic information of each of all bases in a biological sequence fastq file. The characteristic information includes at least a sequence location and a base type of each base in the biological sequence fastq file.

In specific implementation, as shown in FIG. 1, FIG. 1 is a schematic diagram of a biological sequence fastq file according to an embodiment of this application. The biological sequence fastq file includes a file identifier (read ID), a base sequence, +annotation information, and quality scores. The base sequence includes bases of five base types: A, T, C, G, and N. The base sequence in the second line is corresponding to the quality scores in the fourth line, and it indicates that each base is corresponding to one quality score. Characteristic information may include a base type of a base and a sequence location of the base in the biological sequence fastq file, or may include a base type of a base, a sequence location of the base in the biological sequence fastq file, and a quality score of the base. The sequence location includes a row coordinate and a column coordinate.

Optionally, before the characteristic information of each of all the bases in the biological sequence fastq file is obtained, lossy compression may be performed on an original biological sequence fastq file; and an original biological sequence fastq file obtained after the lossy compression is decompressed to obtain the foregoing biological sequence fastq file. A quality score is adjusted after the compressed original biological sequence fastq file is decompressed. According to this method, a compression ratio of the biological sequence fastq file can be further increased.

Optionally, before the characteristic information of each of all the bases in the biological sequence fastq file is obtained, a quality score in an original biological sequence fastq file may be extracted, and lossy compression is performed on the extracted quality score; and a quality score obtained after the lossy compression is decompressed, and the quality score in the original biological sequence fastq file is replaced with the decompressed quality score to obtain the foregoing biological sequence fastq file. The quality score is adjusted after the decompression. According to this method, a compression ratio of the biological sequence fastq file can be further increased.

Optionally, before the characteristic information of each of all the bases in the biological sequence fastq file is obtained, lossy compression may be performed on an original biological sequence fastq file; an original biological sequence fastq file obtained after the lossy compression is decompressed to obtain a fastq file in which both a quality score and an identifier read ID are adjusted; and the adjusted quality score is filtered from the fastq file, and a quality score in the original biological sequence fastq file is replaced with the adjusted quality score to obtain the foregoing biological sequence fastq file. According to this method, a compression ratio of the biological sequence fastq file can be further increased.

A file generation module 602 is configured to: select a target base from all the bases according to a preset rule and the characteristic information of each base, and generate a base patch file by using characteristic information of the target base.

In specific implementation, a base of a target base type may be selected from all the bases as the target base, and the base patch file is generated by using a base type and a sequence location of the target base.

For example, a base of a base type N may be selected, and the base patch file is generated by using the base type N and sequence locations of all bases of the base type N in the biological sequence fastq file. Because a quantity of bases of the base type N is relatively small, a size of the base patch file can be reduced by collecting statistics about characteristic information of the bases of the base type N.

Optionally, the characteristic information further includes a quality score. A base that is of a target base type and whose quality score is different from a preset threshold and/or a base that is not of the target base type and whose quality score is the preset threshold may be selected from all the bases as the target base. The base patch file is generated by using a base type, a quality score, and a sequence location that are of the target base. The preset threshold is a standard quality score of a base of the target base type. For example, a base that is of a base type N and whose quality score is not q and/or a base that is of another type and whose quality score is q may be selected from the biological sequence fastq file as the target base. The base patch file is generated by using a base type, a quality score, and a sequence location that are of the base.

For example, a base that is of a base type N and whose quality score is not q and a base that is of another base type and whose quality score is q may be selected from the biological sequence fastq file as the target bases. The base patch file is generated by using a quality score, a base type, and a sequence location that are of the target base. Because a quantity of bases of the base type N is relatively small, a size of the base patch file can be reduced by collecting statistics about characteristic information of the base that is of the base type N and whose quality score is not q and the base that is of the another base type and whose quality score is q, where q may be but is not limited to 33%.

It should be noted that, in this embodiment of this application, the target base may be selected from all the bases according to multiple preset rules. For example, the target base may be selected from the biological sequence fastq file according to a preset base interval. The base patch file is generated by using a sequence location and a base type of the target base, or the base patch file is generated by using a sequence location, a base type, and a quality score that are of the target base. Alternatively, if several consecutive bases in the biological sequence fastq file are of a same base type, any one of the bases of the same base type may be selected as the target base. The base patch file is generated by using a sequence location and a base type of the target base, or the base patch file is generated by using a sequence location, a base type, and a quality score that are of the target base.

A file compression module 603 is configured to: perform lossless compression on the biological sequence fastq file to obtain a compressed fastq file, and perform lossless compression on the base patch file to obtain a compressed patch file.

In specific implementation, the read ID, the sequence, and the quality score may be separately encoded. The read ID is encoded in an incremental encoding manner. For the sequence, by default, a quality score of a base N is 33% and a quality score of another base is not 33%. When the sequence is being encoded, the base of the base type N is skipped, and other three bases or four bases are combined into one byte for being encoded. For the quality score, a quality score of one base or quality scores of two or three bases are combined into one byte for being encoded. Because a compression ratio is relatively high in this compression algorithm, the compression ratio of the biological sequence fastq file can be increased. In addition, the base patch file may be compressed by using common compression software. For example, the base patch file may be compressed into a compressed patch file in rar or gzip format.

A file decompression module 604 is configured to separately decompress the compressed patch file and the compressed fastq file.

In specific implementation, the compressed patch file and the compressed fastq file may be decompressed by using a method corresponding to the file compression module 603.

An information check module 605 is configured to check whether characteristic information of the target base in the decompressed compressed patch file is consistent with characteristic information of the target base in the decompressed compressed fastq file.

In specific implementation, it may be checked whether a base type corresponding to a sequence location in the decompressed compressed patch file is consistent with a base type corresponding to the sequence location in the decompressed compressed fastq file. If the base type corresponding to the sequence location in the decompressed compressed patch file is consistent with the base type corresponding to the sequence location in the decompressed compressed fastq file, the base type corresponding to the sequence location in the decompressed compressed fastq file may not be processed.

Optionally, it may be checked whether a base type and a quality score that are corresponding to a sequence location in the decompressed compressed patch file are consistent with a base type and a quality score that are corresponding to the sequence location in the decompressed compressed fastq file. If the base types are consistent and the quality scores are also consistent, the base type and the quality score that are corresponding to the sequence location in the decompressed compressed fastq file may not be processed.

An information modification module 606 is configured to: if the characteristic information of the target base in the decompressed compressed patch file is inconsistent with the characteristic information of the target base in the decompressed compressed fastq file, modify the characteristic information of the target base in the decompressed compressed fastq file to the characteristic information of the target base in the decompressed compressed patch file. If only characteristic information of some of target bases in the decompressed compressed fastq file is inconsistent with characteristic information of the some of the target bases in the decompressed compressed patch file, only the characteristic information of the some bases in the decompressed compressed fastq file is replaced.

In specific implementation, if the base type corresponding to the sequence location in the decompressed compressed patch file is inconsistent with the base type corresponding to the sequence location in the decompressed compressed fastq file, the base type corresponding to the sequence location in the decompressed compressed fastq file may be modified to the base type corresponding to the sequence location in the decompressed compressed patch file.

For example, the compressed patch file includes the sequence locations of all the bases of the base type N. After the compressed patch file and the compressed fastq file are separately decompressed, if a sequence location in the decompressed compressed patch file is corresponding to a base type A, but the sequence location in the decompressed compressed fastq file is corresponding to the base type N, the base type N corresponding to the sequence location in the decompressed compressed fastq file may be modified to the base type A. In this way, a base in the decompressed compressed fastq file is adjusted by using the base patch file, so that site precision of the fastq file is improved.

Optionally, if both the base type and the quality score that are corresponding to the sequence location in the decompressed compressed patch file are inconsistent with the base type and the quality score that are corresponding to the sequence location in the decompressed compressed fastq file, the base type corresponding to the sequence location in the decompressed compressed fastq file may be modified to the base type corresponding to the sequence location in the decompressed compressed patch file, and the quality score corresponding to the sequence location in the decompressed compressed fastq file may be modified to the quality score corresponding to the sequence location in the decompressed compressed patch file.

For example, the compressed patch file includes a sequence location, a quality score, and a base type of the base N whose quality score is not q and a sequence location, a quality score, and a base type of another base whose quality score is q. If a sequence location 10 in the decompressed compressed patch file is corresponding to a base type A and a quality score 33%, but the sequence location 10 in the decompressed compressed fastq file is corresponding to a base type N and a quality score 34%, it can be learned, by checking, that both the base type and the quality score that are corresponding to the sequence location 10 in the decompressed compressed patch file are different from the base type and the quality score that are corresponding to the sequence location 10 in the decompressed compressed fastq file. In this case, the base type N corresponding to the sequence location 10 in the decompressed compressed fastq file may be replaced with the base type A, and the quality score 34% corresponding to the sequence location 10 in the decompressed compressed fastq file may be replaced with the quality score 33%.

Figure 7:
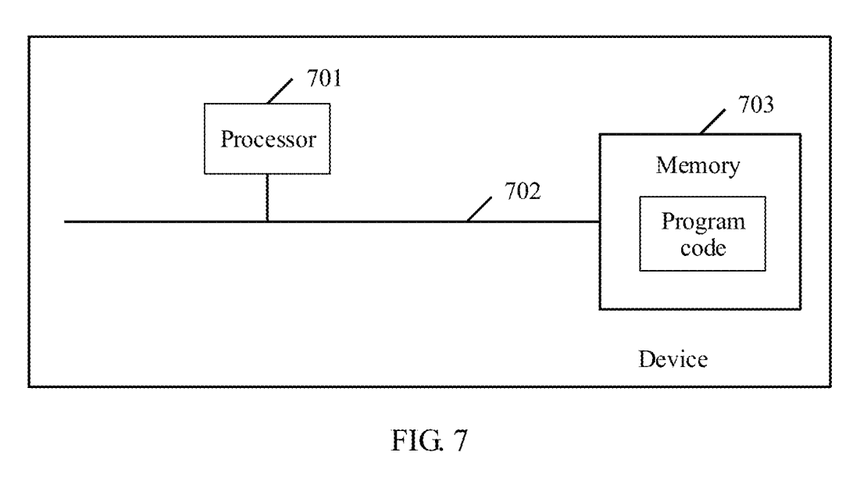
FIG. 7 is a schematic structural diagram of a biological sequence data processing device according to an embodiment of this application.

Further referring to FIG. 7, FIG. 7 is a schematic structural diagram of a biological sequence data processing device according to this application. As shown in the diagram, the device may include at least one processor 701 such as a CPU, at least one memory 703, and at least one communications bus 702. The communications bus 702 is configured to implement connection and communication between these components. The memory 703 may be a high-speed RAM memory, or may be a nonvolatile memory (non-volatile memory), such as at least one magnetic disk memory. Optionally, the memory 703 may be at least one storage apparatus located far away from the processor 701. The device in FIG. 7 may be the biological sequence data processing apparatus shown in FIG. 6. The memory 703 stores a group of program code. The processor 701 executes a program stored in the memory 703, to perform the method performed by the biological sequence data processing apparatus, or to implement functions implemented by the biological sequence data processing apparatus.

It should be noted that, for brief description, the foregoing method embodiments are represented as a series of actions. However, a person skilled in the art should appreciate that this application is not limited to the described order of the actions, because according to this application, some steps may be performed in another order or simultaneously. It should be further appreciated by a person skilled in the art that the embodiments described in this specification all belong to example embodiments, and the involved actions and modules are not necessarily required by this application.

In the foregoing embodiments, the descriptions of the embodiments have respective focuses. For a part that is not described in detail in an embodiment, refer to related descriptions in another embodiment.

A person of ordinary skill in the art may understand that all or some of the steps of the methods in the foregoing embodiments may be implemented by a program instructing relevant hardware. The program may be stored in a computer readable storage medium. The storage medium may include a flash memory, a read-only memory (Read-Only Memory, ROM), a random access memory (Random Access Memory, RAM), a magnetic disk, an optical disc, or the like.

The foregoing describes in detail the biological sequence data processing method and apparatus provided in the embodiments of this application. In this specification, specific examples are applied to describe the principle and implementations of this application. The descriptions of the embodiments are merely intended to help understand the method and core idea of this application. Meanwhile, a person of ordinary skill in the art may, based on the idea of this application, make modifications with respect to the specific implementations and the application scope. Therefore, the content of this specification shall not be construed as a limitation to this application.

What is claimed is:

1. A biological sequence data processing method, wherein the method comprises:
    obtaining characteristic information of each base in a biological sequence fastq file, wherein the characteristic information comprises at least a sequence location and a base type of each base in the biological sequence fastq file;
    selecting a target base from the bases in the biological sequence fastq file according to a preset rule and the characteristic information of each base;
    generating a base patch file by using characteristic information of the target base;
    performing lossless compression on the biological sequence fastq file to obtain a compressed fastq file;
    performing lossless compression on the base patch file to obtain a compressed patch file;
    separately decompressing the compressed patch file and the compressed fastq file;
    determining whether characteristic information of the target base in the decompressed compressed patch file is consistent with characteristic information of the target base in the decompressed compressed fastq file; and
    in response to determining that the characteristic information of the target base in the decompressed compressed patch file is inconsistent with the characteristic information of the target base in the decompressed compressed fastq file, modifying the characteristic information of the target base in the decompressed compressed fastq file to be the same as the characteristic information of the target base in the decompressed compressed patch file, wherein the characteristic information of the target base in the decompressed compressed fastq file is replaced with the characteristic information of the target base in the decompressed compressed patch file.

2. The method according to claim 1, wherein the selecting a target base from the bases in the biological sequence fastq file according to a preset rule and the characteristic information of each base, and the generating a base patch file by using characteristic information of the target base comprise:
    selecting a base of a target base type from the bases in the biological sequence fastq file as the target base; and
    generating the base patch file by using a base type and a sequence location of the target base.

3. The method according to claim 2, wherein the determining whether characteristic information of the target base in the decompressed compressed patch file is consistent with characteristic information of the target base in the decompressed compressed fastq file comprises:
    determining whether a base type corresponding to a sequence location in the decompressed compressed patch file is consistent with a base type corresponding to the sequence location in the decompressed compressed fastq file; and
    wherein the modifying the characteristic information of the target base in the decompressed compressed fastq file to be the same as the characteristic information of the target base in the decompressed compressed patch file comprises:
        modifying the base type corresponding to the sequence location in the decompressed compressed fastq file to be the same as the base type corresponding to the sequence location in the decompressed compressed patch file.

4. The method according to claim 1, wherein the characteristic information further comprises a quality score, and wherein the selecting a target base from the bases in the biological sequence fastq file according to a preset rule and the characteristic information of each base, and the generating a base patch file by using characteristic information of the target base comprise:
    selecting, from the bases in the biological sequence fastq file, a base satisfying at least one of the following as the target base: a base that is of a target base type and whose quality score is different from a preset threshold, and a base that is not of the target base type and whose quality score is the preset threshold; and
    generating the base patch file by using a base type, a quality score, and a sequence location of the target base.

5. The method according to claim 4, wherein the determining whether characteristic information of the target base in the decompressed compressed patch file is consistent with characteristic information of the target base in the decompressed compressed fastq file comprises:
    determining whether a base type and a quality score that are corresponding to a sequence location in the decompressed compressed patch file are consistent with a base type and a quality score that are corresponding to the sequence location in the decompressed compressed fastq file; and
    wherein the modifying the characteristic information of the target base in the decompressed compressed fastq file to be the same as the characteristic information of the target base in the decompressed compressed patch file comprises at least one of:
        modifying the base type corresponding to the sequence location in the decompressed compressed fastq file to be the same as the base type corresponding to the sequence location in the decompressed compressed patch file; and
        modifying the quality score corresponding to the sequence location in the decompressed compressed fastq file to be the same as the quality score corresponding to the sequence location in the decompressed compressed patch file.

6. A biological sequence data processing device, comprising:
    at least one processor; and
    a non-transitory computer-readable storage medium coupled to the at least one processor and storing programming instructions for execution by the at least one processor, the programming instructions instruct the at least one processor to perform the following operations:
        obtaining characteristic information of each base in a biological sequence fastq file, wherein the characteristic information comprises at least a sequence location and a base type of each base in the biological sequence fastq file;
        selecting a target base from the bases in the biological sequence fastq file according to a preset rule and the characteristic information of each base;
        generating a base patch file by using characteristic information of the target base;
        performing lossless compression on the biological sequence fastq file to obtain a compressed fastq file;
        performing lossless compression on the base patch file to obtain a compressed patch file;
        separately decompressing the compressed patch file and the compressed fastq file;

determining whether characteristic information of the target base in the decompressed compressed patch file is consistent with characteristic information of the target base in the decompressed compressed fastq file; and in response to determining that the characteristic information of the target base in the decompressed compressed patch file is inconsistent with the characteristic information of the target base in the decompressed compressed fastq file, modifying the characteristic information of the target base in the decompressed compressed fastq file to be the same as the characteristic information of the target base in the decompressed compressed patch file, wherein the characteristic information of the target base in the decompressed compressed fastq file is replaced with the characteristic information of the target base in the decompressed compressed patch file.

7. The device according to claim 6, wherein the programming instructions further instruct the at least one processor to perform the following operation steps:

selecting a base of a target base type from the bases in the biological sequence fastq file as the target base; and generating the base patch file by using a base type and a sequence location of the target base.

8. The device according to claim 7, wherein the programming instructions further instruct the at least one processor to perform the following operation steps:

determining whether a base type corresponding to a sequence location in the decompressed compressed patch file is consistent with a base type corresponding to the sequence location in the decompressed compressed fastq file; and in response to determining that the base type corresponding to the sequence location in the decompressed compressed patch file is inconsistent with the base type corresponding to the sequence location in the decompressed compressed fastq file, modifying the base type corresponding to the sequence location in the decompressed compressed fastq file to be the same as the base type corresponding to the sequence location in the decompressed compressed patch file.

9. The device according to claim 6, wherein the characteristic information further comprises a quality score, and the programming instructions further instruct the at least one processor to perform the following operation steps:

selecting, from the bases in the biological sequence fastq file, a base satisfying at least one of the following as the target base: a base that is of a target base type and whose quality score is different from a preset threshold, and a base that is not of the target base type and whose quality score is the preset threshold; and generating the base patch file by using a base type, a quality score, and a sequence location of the target base.

10. The device according to claim 9, wherein the programming instructions further instruct the at least one processor to perform the following operation steps:

determining whether a base type and a quality score that are corresponding to a sequence location in the decompressed compressed patch file are consistent with a base type and a quality score that are corresponding to the sequence location in the decompressed compressed fastq file; and in response to determining that the base type and the quality score that are corresponding to the sequence location in the decompressed compressed patch file are inconsistent with the base type and the quality score that are corresponding to the sequence location in the decompressed compressed fastq file, performing at least one of:

modifying the base type corresponding to the sequence location in the decompressed compressed fastq file to be the same as the base type corresponding to the sequence location in the decompressed compressed patch file; and modifying the quality score corresponding to the sequence location in the decompressed compressed fastq file to be the same as the quality score corresponding to the sequence location in the decompressed compressed patch file.

11. A non-transitory computer readable storage medium, wherein the computer readable storage medium includes instructions, when at least one processor of a computing device executes the instructions, the computing device performs the following operations:

obtaining characteristic information of each base in a biological sequence fastq file, wherein the characteristic information comprises at least a sequence location and a base type of each base in the biological sequence fastq file;

selecting a target base from the bases in the biological sequence fastq file according to a preset rule and the characteristic information of each base;

generating a base patch file by using characteristic information of the target base;

performing lossless compression on the biological sequence fastq file to obtain a compressed fastq file;

performing lossless compression on the base patch file to obtain a compressed patch file;

separately decompressing the compressed patch file and the compressed fastq file;

determining whether characteristic information of the target base in the decompressed compressed patch file is consistent with characteristic information of the target base in the decompressed compressed fastq file; and in response to determining that the characteristic information of the target base in the decompressed compressed patch file is inconsistent with the characteristic information of the target base in the decompressed compressed fastq file, modifying the characteristic information of the target base in the decompressed compressed fastq file to be the same as the characteristic information of the target base in the decompressed compressed patch file, wherein the characteristic information of the target base in the decompressed compressed fastq file is replaced with the characteristic information of the target base in the decompressed compressed patch file.

12. The non-transitory computer readable storage medium according to claim 11, wherein the computing device further performs the following operation steps:

selecting a base of a target base type from the bases in the biological sequence fastq file as the target base; and generating the base patch file by using a base type and a sequence location of the target base.

13. The non-transitory computer readable storage medium according to claim 12, wherein the computing device further performs the following operation steps:

determining whether a base type corresponding to a sequence location in the decompressed compressed patch file is consistent with a base type corresponding to the sequence location in the decompressed compressed fastq file; and in response to determining that the base type corresponding to the sequence location in the decompressed compressed patch file is inconsistent with the base type corresponding to the sequence location in the decompressed compressed fastq file, modifying the base type corresponding to the sequence location in the decompressed compressed fastq file to be the same as the base type corresponding to the sequence location in the decompressed compressed patch file.

14. The non-transitory computer readable storage medium according to claim 11, wherein the characteristic information further comprises a quality score, and the computing device further performs the following operation steps:

selecting, from the bases in the biological sequence fastq file, a base satisfying at least one of the following as the target base: a base that is of a target base type and whose quality score is different from a preset threshold, and a base that is not of the target base type and whose quality score is the preset threshold; and generating the base patch file by using a base type, a quality score, and a sequence location of the target base.

15. The non-transitory computer readable storage medium according to claim 14, wherein the computing device further performs the following operation steps:

determining whether a base type and a quality score that are corresponding to a sequence location in the decompressed compressed patch file are consistent with a base type and a quality score that are corresponding to the sequence location in the decompressed compressed fastq file; and in response to determining that the base type and the quality score that are corresponding to the sequence location in the decompressed compressed patch file are inconsistent with the base type and the quality score that are corresponding to the sequence location in the decompressed compressed fastq file, performing at least one of:

modifying the base type corresponding to the sequence location in the decompressed compressed fastq file to be the same as the base type corresponding to the sequence location in the decompressed compressed patch file; and modifying the quality score corresponding to the sequence location in the decompressed compressed fastq file to be the same as the quality score corresponding to the sequence location in the decompressed compressed patch file.

* * * * *